United States Patent [19]

Horstmann et al.

[11] 4,265,898

[45] May 5, 1981

[54] IMIDAZO[2,1-b]-[1,3,4]-THIADIAZOLE COMPOUNDS, COMPOSITION AND THEIR MEDICINAL USE

[75] Inventors: Harald Horstmann, Wuppertal, Fed. Rep. of Germany; Karl-August Meng, deceased, late of Wuppertal, Fed. Rep. of Germany, by Ilse Heide Frieda Meng, legal representative; by Matthias Meng, legal representative, wuppertal, Fed. Rep. of Germany; Friedel Seuter, Wuppertal, Fed. Rep. of Germany; Eike Möller, Wuppertal, Fed. Rep. of Germany

[73] Assignee: Bayer Aktiengesellschaft, Leverkusen, Fed. Rep. of Germany

[21] Appl. No.: 37,626

[22] Filed: May 10, 1979

[30] Foreign Application Priority Data

May 31, 1978 [DE] Fed. Rep. of Germany ....... 2823686

[51] Int. Cl.$^3$ .................... A61K 31/41; C07D 513/04

[52] U.S. Cl. ..................................... 424/270; 544/133; 546/199; 546/271; 546/278; 548/126; 548/138; 548/141; 548/185; 424/248.51; 424/263; 424/267

[58] Field of Search .......................... 424/270; 548/126

[56]  References Cited

U.S. PATENT DOCUMENTS

| 3,726,891 | 4/1973 | Pilgram et al. ........................... 71/90 |
| 3,804,823 | 4/1974 | Fisher et al. ........................... 548/126 |
| 4,042,372 | 8/1977 | Harper ..................................... 71/90 |

FOREIGN PATENT DOCUMENTS 1464259  2/1977  United Kingdom .................... 548/126

Primary Examiner—Donald G. Daus
Assistant Examiner—James H. Turnipseed
Attorney, Agent, or Firm—Sprung, Felfe, Horn, Lynch & Kramer

[57]  ABSTRACT

The present invention relates to certain new imidazo [2,1-b]-[1,3,4]-thiadiazole compounds, to the provision of pharmaceutical compositions containing said compounds and to the use of said compounds and compositions as antithrombotic agents and thrombolytic agents.

21 Claims, No Drawings

IMIDAZO[2,1-b]-[1,3,4]-THIADIAZOLE COMPOUNDS, COMPOSITION AND THEIR MEDICINAL USE

The present relates to certain new imidazo[2,1-b]-[1,3,4]-thiadiazole compounds, to a process for their production and to their use as agents affecting thrombi, e.g., as antithrombotic agents and thrombolytic agents.

It has already been disclosed that some imidazo-[2,1-b[-[1,3,4]-thiadiazole derivatives have chemotherapeutic properties, in particular antimicrobial properties. (Compare Matsukawa and Ban, J. Pharm. Soc. Japan 72, 610 (1952)-C.A. 47,6409 (1953); Matsukawa et al., J. Pharm. Soc. Japan 73, 159 (1953)-C.A. 47, 11185 (1950); Ban, J. Pharm. Soc. Japan 74, 658 (1954)-C.A. 48, 10740 (1954); and Ban, J. Pharm. Soc. Japan 74, 1044 (1954)- C.A. 49, 11630 (1955)).

However, their use as antithrombotic agents or antiphlogistic agents is new and has not yet been disclosed.

According to the present invention we provide compounds which are imidazo[2,1-b]-[1,3,4]-thiadiazoles of the general formula

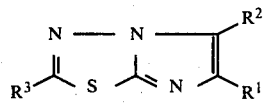

(I)

in which $R^1$ denotes an aryl radical which optionally contains 1 or 2 identical or different substituents selected from halogen, trifluoromethyl, alkyl, alkenyl, phenyl, alkoxy, nitro, cyano, sulphonamido and $SO_n$-alkyl (n is 0, 1 or 2), $R^2$ denotes a hydrogen atom, an alkyl or alkenyl group or an aryl radical which is optionally substituted by halogen, alkyl alkenyl or alkoxy, and $R^3$ denotes a naphthyl, furyl, thienyl or pyridyl radical, which is optionally substituted by 1 or 2 alkyl radicals, or a radical of the general formula

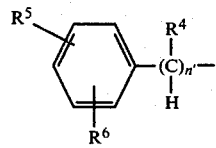

(Ia)

in which n' is 0 or 1, $R^4$ denotes a hydrogen atom or a methyl group, $R^5$ denotes a halogen atom, an alkyl, alkenyl, phenyl or trifluoromethyl radical, a hydroxyl, alkoxy or $SO_{n''}$-alkyl group (n'' is 0, 1 or 2), an acyloxy group, an alkoxylenecarbonyl or alkoxylenecarbalkoxy radical or a nitro, cyano, carboxyl or carbalkoxy group, and $R^6$ denotes a hydrogen or halogen atom or an alkyl, alkenyl or alkoxy group.

The compounds of the invention may be produced when (A) a carbonyl compound of the general formula

(II)

or an enamine, enol ester or enol ether thereof, in which $R^1$ and $R^2$ having the meaning indicated above, and X denotes a leaving group, preferably halogen, hydroxyl, alkoxy, acyloxy, alkyl, arylsulphonyloxy, quaternary ammonium or tertiary phosphonium or sulphonium, is reacted with a 2-amino-1,3,4-thiadiazole of the general formula

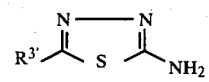

(III)

in which $R^{3'}$ denotes a naphthyl, furyl, thienyl or pyridyl radical, which is optionally substituted by 1 or 2 alkyl radicals, or a substituent of the general formula

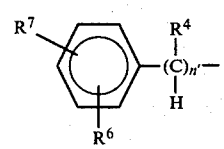

(Ib)

wherein n', $R^4$ and $R^6$ have the meaning indicated above, and $R^7$ denotes a halogen atom or an alkyl, alkenyl, phenyl, trifluoromethyl, hydroxyl, alkoxy, $SO_n$-alkyl (n is 0, 1 or 2), nitro or cyano group, optionally in the presence of inert solvents and basic auxiliaries at temperatures between 30° and 230° C., and, if desired, in a subsequent reaction, in compounds of the general formula I in which (a) $R^5$ represents a hydroxyl group, this hydroxyl group is alkylated or acylated in a manner which is in itself known or (b) in the case where $R^5$ denotes a nitrile group, this nitrile group is saponified to the carboxyl group in a manner which is in itself known and the carboxyl group is then optionally saponified to a carbalkoxy group, or (B) when 1-acylamino-2-mercapto-imidazoles of the general formula IV

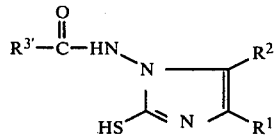

(IV)

in which $R^1$, $R^2$ and $R^{3'}$ have the meaning indicated above, are cyclised with agents which split off water, preferably with inorganic acid halides, more preferably with phosphorus oxychloride, at temperatures between 30° and 200° C. and optionally under increased pressure.

The preparation of the compounds of the present invention can be represented by the equation which follows, depending on the nature of the method and of the starting substances used, 2-(4-chlorophenyl)-6-phenyl-imidazo-[2,1-b]-[1,3,4]-thiadiazole having been chosen as an example:

Equation:

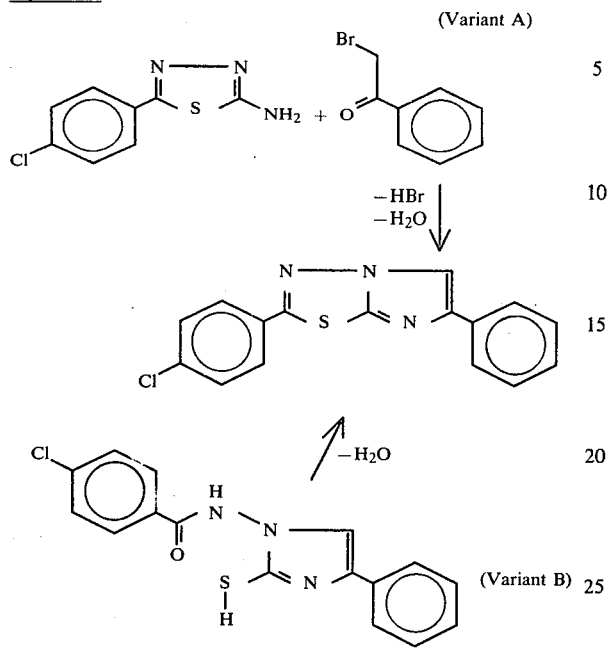

In the reaction of the carbonyl compound of the formula (II) with the 2-amino-1,3,4-thiadiazole of the formula (III), the compound of the general formula

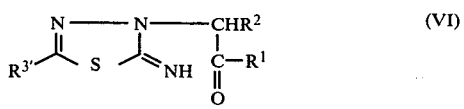

is formed as an intermediate, this imide, in the case where the leaving radical X is the radical of a strong acid, being obtained as the corresponding ammonium salt of the formula

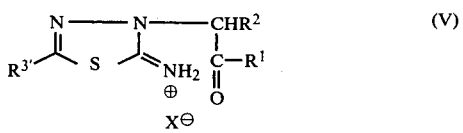

These intermediate stages can be isolated, if appropriate, and cyclised in the customary manner in a second reaction step to give the compounds of the formula (I) according to the invention. However, it is of particular interest to carry out the reaction of compounds of the formula (II) with compounds of the formula (III) in a single stage and to carry out the cyclisation directly, without isolating the intermediate stages, in particular using high-boiling solvents.

Basic auxiliaries which can be employed in the reaction of compounds of formula (II) with compounds of formula (III) are preferably alkali metal hydroxides or alkaline earth metal hydroxides, such as sodium hydroxide, potassium hydroxide or calcium hydroxide, alkali metal carbonates and alkaline earth metal carbonates, such as sodium carbonate, sodium bicarbonate, potassium carbonate and calcium carbonate, or organic bases, such as triethylamine or pyridine.

Compounds of the formula (I) in which $R^5$ denotes an acyloxy group are advantageously prepared by acylating corresponding compounds of the formula (I) in which $R^5$ represents hydroxyl with acid anhydrides or acid chlorides in a manner which is in itself known.

Compounds in which $R^5$ represents an alkoxyenecarboxyl or alkoxylenecarbalkoxy group are obtained from the corresponding hydroxy compounds of the formula (I) by reaction with α-halogenocarboxylic acids or α-halogenocarboxylic acid esters in a manner which is in itself known, if appropriate in the presence of basic condensing agents.

Compounds of the general formula (I) in which $R^5$ denotes a carboxyl group are preferably prepared by saponifying the corresponding nitrile compound or by hydrolysing the corresponding carbalkoxy compounds.

On the other hand, the corresponding carbalkoxy compounds can be obtained from the compounds in which $R^5$ represents a carboxyl group by esterification processes which are generally customary and known, by reaction with appropriate alcohols.

Unless expressly indicated otherwise, halogen represents fluorine, chlorine or bromine.

Alkyl preferably represents straight-chain, branched or cyclic alkyl with up to 6 carbonatoms, the alkylene chain optionally being interrupted by oxygen.

Alkenyl preferably represents straight-chain, branched or cyclic alkenyl with 1 or 2 unsaturated bonds and up to 6 carbon atoms, one $CH_2$ group optionally being replaced by oxygen.

Alkoxy preferably represents such straight or branched chain substituents having up to 6 carbon atoms. Aryl preferably represents mono- or bi-cyclic carbocyclic aryl, such as phenyl, biphenyl or naphthyl optionally substituted by one or two substituents as indicated above.

The acyl radical in the claimed acyloxy groups preferably represents an alkanoyl radical with 1 to 4 carbon atoms or an optionally substituted benzoyl radical.

The nitrogen atom of the sulphonamido group is preferably unsubstituted or substituted by 1 or 2 alkyl radicals with 1 to 4 carbon atoms, the two alkyl radicals optionally forming a 5- to 8-membered ring which contains 1 or 2 identical or different hetero-atoms from the group comprising oxygen, sulphur and N-Z, Z representing an alkyl group with 1 to 4 carbon atoms or an optionally substituted phenyl radical.

An "alkoxylenecarboxyl" group, preferably denotes a substituent of the formula

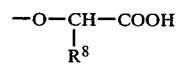

and an "alkoxylenecarbalkoxy" group preferably denotes a substituent of the formula

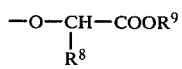

in which $R^8$ denotes a hydrogen atom or a straight-chain or branched alkyl radical with 1 to 4 carbon atoms, and $R^9$ denotes a straight-chain or branched alkyl radical with 1 to 4 carbon atoms.

A "carbalkoxy" group, preferably denotes a substituent of th formula

in which $R^9$ has the meaning indicated above.

By furyl, thienyl, pyridyl and naphthyl, there are preferably understood those radicals which are linked in the α- or β-position.

Preferably, in the formulae (I) and (II), $R^1$ denotes an aryl radical which optionally substituted by one or two identical or different substituents selected from halogen, such as fluorine, chlorine or bromine, trifluoromethyl, alkyl with 1 to 6 carbon atoms, in particular methyl, ethyl, propyl, isopropyl or butyl, allyl, alkoxy or $SO_n$-alkyl (n is 0, 1 or 2) with 1 to 4 carbon atoms, in particular methoxy, ethoxy, propoxy, methylmercapto, ethylmercapto, propylmercapto, isopropylmercapto, methylsulphinyl, methylsulphonyl or ethylsulphonyl, phenyl, nitro, cyano, sulphonamido with an optionaly substituted N atom, such as N-methylsulphonamido or N-dimethylsulphonamido, and sulphonamido, the N atom of which is a member of a 5 to 7 membered heterocyclic ring, such as pyrrolidino, piperidino or hexamethyleneimino and which optionally can contain further hetero-atoms, such as oxygen or an N atom substituted by a methyl or phenyl group, $R^2$ denotes a hydrogen atom, an alkyl radical, such as methyl, ethyl, propyl or isopropyl, or an aryl radical, which can be unsubstituted or substituted by a halogen atom, such as fluorine or chlorine, an alkyl radical, such as methyl or ethyl, or an alkoxy group, such as methoxy or ethoxy, X represents halogen, such as chlorine, bromine or iodine, acyloxy, such as formyloxy, acetoxy, propionyloxy, ethoxycarbonyloxy or benzoyloxy, alkyl- or aryl-sulphonyloxy, such as methylsulphonyloxy (mesyloxy) or toluenesulphonyloxy (tosyloxy), or quaternary ammonium, such as pyridinium or trialkylammonium, such as trimethylammonium. Preferably, in the formula (I), $R^3$ represents α- or β-naphthyl, an α- or β-furyl radical, which can be substituted by one or two alkyl radicals, such as methyl or ethyl, an α- or β-thienyl radical, which can be substituted by one or two alkyl radicals, such as methyl or ethyl, an α- or β-pyridyl radical, which can be substituted by alkyl, such as methyl or ethyl, or a substitutent of the formula (Ia) as given above, in which n' and $R^4$ have the above mentioned meanings and $R^5$ denotes a substituent selected from halogen, such as fluorine, chlorine or bromine, alkyl, such as methyl, ethyl, propyl, isopropyl, butyl or tert.-butyl, allyl, phenyl, trifluoromethyl, hydroxyl, alkoxy, such as methoxy, ethoxy, propoxy or isopropoxy, $SO_n$-alkyl (n=0-2), such as methylmercapto, isopropylmercapto, methylsulphinyl, methylsulphonyl or ethylsulphonyl, acyloxy, such as formyloxy, acetoxy or propionyloxy, alkoxylene-carboxyl, such as oxymethylenecarboxyl or α-oxyethylenecarboxyl, oxyalkylenecarbalkoxy, such as oxymethylenecarbomethoxy, oxymethylenecarboethoxy, α-oxyethylenecarbomethoxy or α-oxyethylenecarboethoxy, nitro, cyano, carboxyl and carbalkoxy, such as carbomethoxy, carboethoxy or carbopropoxy, and $R^6$ denotes hydrogen or a further substituent from the group comprising halogen, such as chlorine or bromine, alkyl, such as methyl, ethyl, propyl or butyl, and an alkoxy radical, such as methoxy or ethoxy.

Compounds of the general formula (I), according to the invention, wherein $R^1$ represents phenyl, which is optionally substituted by fluorine, chlorine, methyl, tert.-butyl, phenyl, trifluoromethyl, methoxy, methylmercapto, methylsulphonyl or the

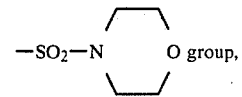

$R^2$ represents hydrogen or a methyl or phenyl radical and $R^3$ denotes α- or β-naphthyl, α- or β-furyl or -thienyl or α- or β-pyridyl, it being possible for the heterocyclic radicals to be substituted by a methyl group, or a radical of the formula (Ia) given previously wherein n' is 0 or 1, $R^4$ denotes hydrogen or a methyl group, $R^5$ denotes methyl, ethyl, propyl, isopropyl, trifluoromethyl, fluorine, chlorine or bromine, hydroxyl, methoxy, ethoxy or propoxy, oxymethylenecarboxyl, oxymethylenecarbomethoxy, oxymethylenecarboethoxy, α-oxyethylenecarboxyl, α-oxyethylenecarbomethoxy, α-oxyethylenecarboethoxy, methylmercapto, methylsulphonyl, acetoxy, propionyloxy, nitro, cyano, carboxyl, carbomethoxy or carboethoxy and $R^6$ denotes hydrogen, methyl or ethyl, fluorine, chlorine, methoxy or ethoxy, are of particular importance.

In the formulae (III) and (IV), $R^{3'}$ preferably represents naphthyl, furyl, thienyl or pyridyl, in each case linked in the α- or β-position, the heterocyclic rings optionally being substituted by a methyl group, or the radical of the formula (Ia) given previously wherein n' is 0 or 1, $R^4$ denotes hydrogen or a methyl group, $R^5$ represents alkyl with 1 to 4 carbon atoms, trifluoromethyl, fluorine, chlorine, bromine, hydroxyl, alkoxy with 1 to 4 carbon atoms, methylmercapto, methylsulphonyl, nitro and cyano and $R^6$ represents hydrogen, alkyl or alkoxy with in each case 1 to 2 carbon atoms, fluorine or chlorine.

The thiadiazoles of the formula (III) used as starting materials are known, or they can be prepared by known methods (literature: Freund and Meinecke, Ber. 29, 2511 (1896); and Yound and Eyre, J. Chem. Soc. 79, 54 (1901)).

The following are examples of thiazoles of formula (III):

2-Amino-5-[3-methyl-fur-2-yl]-1,3,4-thiadiazole, 2-amino-5-[4-methyl-fur-2-yl]-1,3,4-thiadiazole, 2-amino-5-[5-methyl-fur-2-yl]-1,3,4-thiadiazole, 2-amino-5-[2-methyl-fur-3-yl]-1,3,4-thiadiazole, 2-amino-5-[4-methyl-fur-3-yl]-1,3,4-thiadiazole, 2-amino-5-[5-methyl-fur-3-yl]-1,3,4-thiadiazole, 2-amino-5-[3,4,-dimethyl-fur-2-yl]-1,3,4-thiadiazole, 2-amino-5-[3,5-dimethyl-fur-2-yl]-1,3,4-thiadiazole, 2-amino-5-[3-methyl-thien-2-yl]-1,3,4-thiadiazole, 2-amino-5-[4-methyl-thien-2-yl]-1,3,4-thiadiazole, 2-amino-5-[5-methyl-thien-2-yl]-1,3,4-thiadiazole, 2-amino-5-[2-methyl-thien-3-yl]-1,3,4-thiadiazole, 2-amino-5-[4-methyl-thien-3-yl]-1,3,4-thiadiazole, 2-amino-5-[5-methyl-thien-3-yl]-1,3,4-thiadiazole, 2- amino-5-[3,4-dimethyl-thien-2-yl]-1,3,4-thiadiazole,
2-amino-5-[3,5-dimethyl-thien-2-yl]-1,3,4-thiadiazole,
2-amino-5-[2,5-dimethyl-thien-3-yl]-1,3,4-thiadiazole,
2-amino-5-[4,5-dimethyl-thien-2-yl]-1,3,4-thiadiazole,
2-amino-5-[4,5-dimethyl-fur-2-yl]-1,3,4-thiadiazole,
2-amino-5-[2,4-dimethyl-thien-3-yl]-1,3,4-thiadiazole,
2-amino-5-[2,4-dimethyl-fur-3-yl]-1,3,4-thiadiazole,
2-amino-5-[4,5-dimetyl-thien-3-yl]-1,3,4-thiadiazole,
2-amino-5-[4,5,-dimethyl-fur-3-yl]-1,3,4-thiadiazole,
2-amino-5-[2,5-dimethyl-fur-3-yl]-1,3,4-thiadiazole,
2-amino-5-[3-methyl-pyrid-2-yl]-1,3,4-thiadiazole,
2-amino-5-[4-methyl-pyrid-2-yl]-1,3,4-thiadiazole,
2-amino-5-[5-methyl-pyrid-3-yl]-1,3,4-thiadiazole,
2-amino-5-[6-methyl-pyrid-2-yl]-1,3,4-thiadiazole,
2-amino-5-[2-methyl-pyrid-3-yl]-1,3,4-thiadiazole,
2-amino-5-[5-methyl-pyrid-3-yl]-1,3,4-thiadiazole,
2-amino-5-[6-methyl-pyrid-3-yl]-1,3,4-thiadiazole,
2-amino-5-[3,4-dimethyl-pyrid-2-yl]-1,3,4-thiadiazole,
2-amino-5-[2,4-dimethyl-pyrid-3-yl]-1,3,4-thiadiazole,
2-amino-5-(2-methyl-phenyl)-1,3,4-thiadiazole, 2-amino-5-(2-ethyl-phenyl)-1,3,4-thiadiazole, 2-amino-5-(2-isopropylphenyl)-1,3,4-thiadiazole, 2-amino-5-(3-methyl-phenyl)-1,3,4-thiadiazole, 2-amino-5-(3-butyl-phenyl)-1,3,4-thiadiazole, 2-amino-5-(4-methyl-phenyl)-1,3,4-thiadiazole, 2-amino-5-(2,3-dimethyl-phenyl)-1,3,4-thiadiazole, 2-amino-5-(2,4-dimethyl-phenyl)-1,3,4-thiadiazole, 2-amino-5-(2,6-dimethyl-phenyl)-1,3,4-thiadiazole, 2-amino-5-(2-methyl-5-ethylphenyl)-1,3,4-thiadiazole, 2-amino-5-(2-chloro-phenyl)-1,3,4-thiadiazole, 2-amino-5-(2-fluoro-phenyl)-1,3,4-thiadiazole, 2-amino-5-(3-bromo-phenyl)-1,3,4-thiadiazole, 2-amino-5-(4-chloro-phenyl)-1,3,4-thiadiazole, 2-amino-5-(4-phenyl-phenyl)-1,3,4-thiadiazole, 2-amino-5-(3-trifluoromethyl)-1,3,4-thiadiazole, 2-amino-5-(4-trifluoromethyl)-1,3,4-thiadiazole, 2-amino-5-(2-hydroxy-phenyl)-1,3,4-thiadiazole, 2-amino-5-(2-acetoxy-phenyl)-1,3,4-thiadiazole, 2-amino-5-(3-hydroxy-phenyl)-1,3,4-thiadiazole, 2-amino-5-(4-hydroxy-phenyl)-1,3,4-thiadiazole, 2-amino-5-(2-methoxy-phenyl)-1,3,4-thiadiazole, 2-amino-5-(3-methoxy-phenyl)-1,3,4-thiadiazole, 2-amino-5-(4-methoxy-phenyl)-1,3,4-thiadiazole, 2-amino-5-(2-ethoxy-phenyl)-1,3,4-thiadiazole, 2-amino-5-(3-isopropoxy-phenyl)-1,3,4-thiadiazole, 2-amino-5-(4-butoxy-phenyl)-1,3,4-thiadiazole, 2-amino-5-(2-methylmercapto-phenyl)-1,3,4-thiadiazole, 2-amino-5-(2-methylsulphonyl-phenyl)-1,3,4-thiadiazole, 2-amino-5-(3-methylmercapto-phenyl)-1,3,4-thiadiazole, 2-amino-5-(4-ethylmercapto-phenyl)-1,3,4-thiadiazole, 2-amino-5-(4-ethylsulphonyl-phenyl)-1,3,4-thiadiazole, 2-amino-5-(2-methylsulphinyl-phenyl)-1,3,4-thiadiazole, 2-amino-(2-nitro-phenyl)-1,3,4-thiadiazole, 2-amino-(3-nitro-phenyl)-1,3,4-thiadiazole, 2-amino-(2-cyano-phenyl)-1,3,4-thiadiazole, 2-amino-(3-cyano-phenyl)-1,3,4-thiadiazole, 2-amino-(4-cyano-phenyl)-1,3,4-thiadiazole, 2-amino-(2-methyl-4-chloro-phenyl)-1,3,4-thiadiazole, 2-amino-(2-methyl-5-chloro-phenyl)-1,3,4-thiadiazole, 2-amino-(2-methyl-4-fluoro-phenyl)-1,3,4-thiadiazole, 2-amino-(2,4-dimethyl-phenyl)-1,3,4-thiadiazole, 2-amino-(3,4-dimethyl-phenyl)-1,3,4-thiadiazole, 2-amino-(2,6-dimethyl-phenyl)-1,3,4-thiadiazole, 2-amino-(2-chloro-6-methyl-phenyl)-1,3,4-thiadiazole, 2-amino-(2-fluoro-4-methyl-phenyl)-1,3,4-thiadiazole, 2-amino-(2,6-dichlorophenyl)-1,3,4-thiadiazole, 2-amino-(2,4-dichloro-phenyl)-1,3,4-thiadiazole, 2-amino-(3,5-dichloro-phenyl)-1,3,4-thiadiazole, 2-amino-(2-hydroxy-4-methyl-phenyl)-1,3,4-thiadiazole, 2-amino-(2-hydroxy-4-chloro-phenyl)-1,3,4-thiadiazole, 2-amino-(2-acetoxy-4-chloro-phenyl)-1,3,4-thiadiazole, 2-amino-(3-acetoxy-4-methyl-phenyl)-1,3,4-thiadiazole, 2-amino-(3-methylmercapto-4-chloro-phenyl)-1,3,4-thiadiazole, 2-amino-(3,4-dimethoxy-phenyl)-1,3,4-thiadiazole, 2-amino-(2,4-dimethoxy-phenyl)-1,3,4-thiadiazole, 2-amino-(2-methoxy-4-chloro-phenyl)-1,3,4-thiadiazole, 2-amino-(2-methyl-4-methoxy-phenyl)-1,3,4-thiadiazole, 2-amino-(2-nitro-4-chloro-phenyl)-1,3,4-thiadiazole, 2-amino-(2-methyl-4-nitro-phenyl)-1,3,4-thiadiazole, 2-amino-5-(2-methyl-benzyl)-1,3,4-thiadiazole, 2-amino-5-(2-chloro-benzyl)-1,3,4-thiadiazole, 2-amino-5-(α-methyl-2,6-dichloro-benzyl)-1,3,4-thiadiazole, 2-amino-5-(3,4-dichloro-benzyl)-1,3,4-thiadiazole, 2-amino-5-(4-chloro-benzyl)-1,3,4-thiadiazole, 2-amino-5-(2-methoxy-benzyl)-1,3,4-thiadiazole, 2-amino-5-(4-nitro-benzyl)-1,3,4-thiadiazole, 2-amino-5-(2-methyl-4-chloro-benzyl)-1,3,4-thiadiazole and 2-amino-5-(α-methyl-3,4-dimethyl-benzyl)-1,3,4-thiadiazole.

The carbonyl compounds of the general formula II used as a starting material are known, or they can be obtained by methods which are known from the literature (compare, for example, Houben-Weyl, Methoden der organischen Chemie (Methods of Organic Chemistry), volume V, 3, pages 615–622; volume V, 4, pages 171–189, Georg Thieme Verlag, Stuttgart 1962 and 1960.

Examples which may be mentioned are: α-chloroacetophenone, α-bromo-acetophenone, phenacyl-N-pyridinium-bromid, α-bromo-2-chloro-acetophenone, α-bromo-3-chloro-acetophenone, α-bromo-4-chloro-acetophenone, α-bromo-3,4-dichloro-acetophenone, α-bromo-4-trifluoromethyl-acetophenone, α-bromo-2-methylmercapto-acetophenone, α-bromo-2-methyl-acetophenone, α-bromo-3-methyl-acetophenone, α-bromo-4-methyl-acetophenone, α-bromo-2-methyl-4-chloro-acetophenone, α-bromo-4-methoxy-acetophenone, α-bromo-3-nitro-acetophenone, α-bromo-4-nitro-acetophenone, α-bromo-4-cyano-acetophenone, α-bromo-4-methylmercapto-acetophenone, α-bromo-4-methylsulphonyl-acetophenone, α-bromo-4-tert.-butyl-acetophenone, α-bromo-4-phenyl-acetophenone, α-bromo-4-bromo-acetophenone, α-bromo-4-fluoro-acetophenone, α-bromo-2-fluoro-acetophenone, α-bromo-propiophenone, α-bromo-4-methyl-propiophenone, α-bromo-3-chloro-propiophenone, α-bromo-3-methyl-propiophenone, α-bromo-α-phenyl-acetophenone (desyl bromide) and α-bromo-α-phenyl-4-chloro-acetophenone.

The 1-acylamino-2-mercapto-imidazoles used as starting substances can be obtained by processes known from the literature (compare T. Pyl et al., Lieb. Ann. d. Chemie 663 (1963), pages 113–119).

Examples which may be mentioned are, inter alia: 1-(2-chlorobenzoylamino)-2-mercapto-4-phenyl-imidazole, 1-(4-chlorobenzoylamino)-2-mercapto-4-phenyl-imidazole, 1-(2-methylbenzoylamino)-2-mercapto-4-phenyl-imidazole, 1-(3-methylbenzoylamino)-2-mercapto-4-phenyl-imidazole, 1-(2-methoxybenzoylamino)-2-mercapto-4-phenyl-imidazole, 1-(2-hydroxybenzoylamino)-2-mercapto-4-phenyl-imidazole, 1-(3-nitrobenzoylamino)-2-mercapto-4-phenyl-imidazole, 1-(2-tri-fluoromethylbenzoylamino)-2-mercapto-4-phenyl-imidazole, 1-(α-furoylamino)-2- mercapto-4-phenyl-imidazole and 1-(α-thenoylamino)-2-mercapto-4-phenyl-imidazole.

All the customary inert organic solvents can be used as diluents in carrying out the processes according to the invention. These solvents include, preferably, hydrocarbons, such as benzene, toluene and xylene, halogenated hydrocarbons, such as methylene chloride, chloroform, carbon tetrachloride and chlorobenzene, alcohols, such as methanol, ethanol, propanol, butanol, benzyl alcohol and glycol mono-methyl ether, ethers, such as tetrahydrofurane, dioxane and glycol dimethyl ether, amides, such as dimethylformamide, dimethylacetamide, N-methyl-pyrrolidone and hexamethylphosphoric acid triamide, sulphoxides, such as dimethylsulphoxide, sulphones, such as sulpholane and bases, such as pyridine, picoline, collidine, lutidine and quinoline.

The reaction temperatures can be varied within a wide range. Preferably the reaction is carried out between 30° and 230° C., preferably between 50° and 180° C. The reaction is carried out under normal pressure, but it can also be carried out at elevated pressure in a closed vessel.

In carrying out the process (variant A) according to the invention, the compounds of the formula (II) and (III) are in each case preferably reacted with one another in equimolar amounts.

The resulting compounds according to the invention are substances which can be used as medicaments. When administered, preferably orally or parenterally, they cause a great reduction in thrombotic deposition and can thus be used for the treatment and prophylaxis of thrombembolic diseases.

As stated above, the invention also relates to the use in human and veterinary medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) absorptive carriers, e.g. kaolin and bentonite; (i) lubricants, e.g talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made in micro-encapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

In the case of parenteral use, solutions of the active compounds, employing suitable liquid excipients, can be used. The fact that the compounds according to the invention, in a suitable solvent, combines with an equimolar amount of a non-toxic inorganic or organic base has proved particularly advantageous in the case of parenteral use. Examples of bases which may be mentioned are: sodium hydroxide solution, potassium hydroxide solution, ethanolamine, diethanolamine, triethanolamine, amino-tris-hydroxy-methyl-methane, glucosamine and N-methylglucosamine.

Salts of this type can also be of increased importance of oral use of the compounds according to the invention, in that they accelerate or delay resorption as required. Examples of salts which may be mentioned, in addition to those already mentioned above, are: magnesium salt, calcium salts, aluminum salt and iron salts.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters)m microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.5 to 90% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for parenteral administration of the medicaments of the invention is 5 to 500 mg of active ingredient, and for oral administration is 25 mg to 5 g of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously) or rectally, preferably orally or parenterally. Preferred pharmaceutical compositions and medicaments are therefore those adapted for administration such as oral or parenteral administration. Administration in the method of the invention is preferably oral or parenteral administration.

In general it has proved advantageous to administer parenterally amounts of from 0.01 mg to 50 mg/kg preferably 0.1 mg to 10 mg/kg of body weight per day and to administer orally amounts of from 0.1 mg to 500 mg/kg, preferably 0.5 mg to 100 mg/kg of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

These statements apply to the use of the compounds according to the invention both in veterinary medicine and medicine for the treatment of warm-blooded animals.

The antithrombotic action of the compounds according to the invention is tested on experimentally produced venous thrombi in rats. These tests show that doses of 10 mg/kg administered perorally already cause an inhibition of the growth of the thrombi of more than 30%. In the case of arterial thrombi of rats, the same dose gave an inhibition of the weight of the thrombi of over 60%.

In addition to this antithrombotic action, the compounds according to the invention also exhibit a thrombolytic action, that is to say, on subsequent administration, they reduce the size of thrombi already present or break the thrombi up again. Corresponding thrombolytic effects could hitherto only be achieved by repeated intravenous administration of toxic fibrinolytic agents, such as streptokinase and urokinase. This advantageous action can already be achieved by one oral administration daily of the compounds according to the invention. The compounds according to the invention thus represent an enrichment of pharmacy.

The preparation of the compounds according to the present invention will now be illustrated in the following Examples.

EXAMPLE 1

(Process variant A)

(a)

2-(α-Furyl)-6-phenyl-imidazo[2,1-b]-1,2,4-thiadiazole

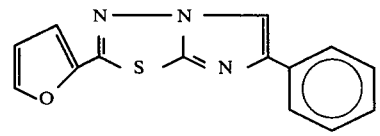

16.7 g (0.1 mol) of 2-amino-5-(α-furyl)-1,3,4-thiadiazole (prepared by oxidation of furfural thiosemicarbazone) together with 20 g of bromoacetophenone are heated to 100° C. in 100 ml of dimethylformamide for 5 hours, whilst stirring. The mixture is cooled, the reaction product which has precipitated is filtered off and the mother liquor is concentrated in a rotary evaporator. The oily residue is triturated with water and, after decanting, the product phase is boiled up in ethanol, whereupon the residue crystallises completely.

The crystals are filtered off and combined with the bulk of the product. A total of 21.2 g (79.5%) of colourless crystals of melting point 190°–192° C. is obtained.

(b) 8.4 g (0.05 mol) of 2-amino-5-(α-furyl)-1,3,4-thiadiazole, together with 10 g of bromoacetophenone, are heated to the boil, under reflux, at 100 ml of acetone for 2 hours, whilst stirring. The mixture is cooled, the precipitate is filtered off and 17 g of colourless crystals, in the form of the hydrobromide, of melting point 219° C. are obtained. The base 2-(α-furyl)-4-(2-phenacyl)-1,3,4-thiadiazol-5-one-imide, liberated with 2 N NaOH, of the formula

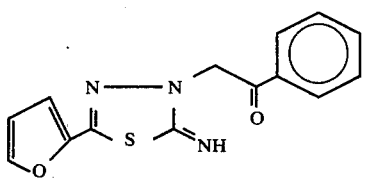

melts at 166° C. (from ethanol).

1. 3.7 g (0.01 mol) of the hydrobromide of melting point 219° C. are heated under reflux in 80 ml of water for 2 hours, whilst stirring. The mixture is cooled and the product which has separated out is filtered off. 2.2 g of colourless crystals (82% of theory) of melting point 190°–192° C., which are identical to the product obtained according to a), are obtained.
2. 5 g of the hydrobromide of melting point 210° C. are warmed to 150° C. in 25 ml of dimethylformamide for 0.5 hour, whilst stirring. The solvent is driven off in a rotary evaporator, the residue is triturated with water, the water is decanted off, the product phase is boiled up with 50 ml of ethanol and the mixture is cooled and filtered. 3.5 g of colourless crystals (96% of theory) of melting point 190°–192° C., which are identical to the product obtained according to a), are obtained.

EXAMPLE 2

2-(α-Furyl)-6-(4-chlorophenyl)-imidazo[2,1-b]-1,3,4-thiadiazole

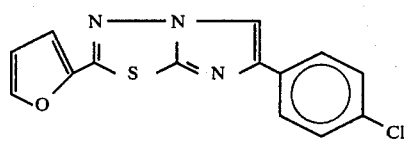

16.7 g (0.1 mol) of 2-amino-5-(α-furyl)-1,3,4-thiadiazole together with 23.4 g of 4-chloro-α-bromoacetophenone are heated to the boil in 100 ml of dimethylformamide for 5 hours, whilst stirring. The mixture is cooled and the precipitate is filtered off and digested in hot methanol. After cooling the digestion mixture, the product is again filtered off, and rinsed with methanol. 22.2 g of colourless crystals of melting point 204° C. are obtained in a yield of 75% of theory.

EXAMPLE 3

2-(α-Furyl)-6-(4-methoxyphenyl)-imidazo[2,1-b]-1,3,4-thiadiazole

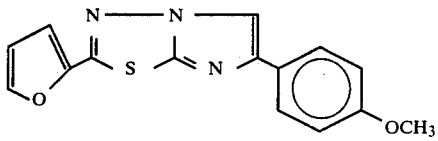

16.7 g (0.1 mol) of 2-amino-5-(α-furyl)-1,3,4-thiadiazole together with 22.8 g of 4-methoxy-α-bromoacetophenone are heated under reflux in 200 ml of dimethylformamide for 3 hours, whilst stirring. The mixture is cooled and the product which has precipitated is filtered off and digested with hot alcohol. 66.5 g, corresponding to 66.5% of theory, of colourless crystals of melting point 197° C. are obtained.

The compounds listed in Table 1 were obtained by an analogous procedure.

TABLE 1

| Example No. | R | R' | F | Yield % of theory |
|---|---|---|---|---|
| 4 | α-furyl | –C$_6$H$_4$–SO$_2$N(morpholino) | 299° C. | 80 |
| 5 | α-furyl | –C$_6$H$_4$–OCH$_3$ | 161° C. | 51 |
| 6 | α-furyl | –C$_6$H$_4$–CH(CH$_3$)$_2$ | 204° | 67 |
| 7 | α-furyl | –C$_6$H$_4$–CH$_3$ (m-) | 130° | 35 |
| 8 | α-furyl | –C$_6$H$_4$–CH$_3$ (o-) | 127° | 57 |
| 9 | α-furyl | –C$_6$H$_4$–CH$_3$ (p-) | 202° | 55 |
| 10 | α-furyl | –C$_6$H$_4$–C$_6$H$_5$ | 260° | 66 |
| 11 | α-furyl | –C$_6$H$_3$Cl$_2$ | 214° | 68 |
| 12 | α-thienyl | –C$_6$H$_5$ | 192° | 70 |
| 13 | 3-methyl-2-thienyl | –C$_6$H$_5$ | 142° | 55 |
| 14 | pyridyl | –C$_6$H$_5$ | 237° | 73 |

TABLE 1-continued

Structure: R-C(=N-N)-S-C(=N)-CH=CH-R' (imidazo[2,1-b]-1,3,4-thiadiazole with H on ring)

| Example No. | R | R' | F | Yield % of theory |
|---|---|---|---|---|
| 15 | 3-pyridyl | phenyl | 217° | 10 |

EXAMPLE 16

2-(2-Chlorophenyl)-6-phenyl-imidazo[2,1-b]-1,3,4-thiadiazole

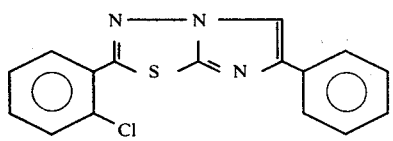

10.5 g (0.05 mol) of 2-amino-5-(2-chlorophenyl)-1,3,4-thiadiazole, melting point 189,5° C. (prepared by reacting thiosemicarbazide with 2-chlorobenzoyl chloride) together with 10 g (0.05 mol) of bromoacetophenone are warmed to 120° C. in 100 ml of dimethylformamide for 3 hours and the mixture is then cooled and concentrated in a rotary evaporator. After digesting the residue with water, the digestion mixture is filtered and the residue is recrystallised from alcohol. A second fraction is obtained by concentrating the alcoholic mother liquor. A total yield of 12.5 g, corresponding to 80% of theory, of colourless crystals of melting point 126° C. is obtained.

The following 2-aryl-6-phenyl-imidazo[2,1-b]-1,3,4-thiadiazoles in Table 2 were obtained by an analogous procedure:

TABLE 2

| Example No. | R | F | Yield % of theory |
|---|---|---|---|
| 17 | 3-chlorophenyl | 191° | 70 |
| 18 | 4-chlorophenyl | 260° | 72 |
| 19 | 2-nitrophenyl | 182° C. | 45 |
| 20 | 4-nitrophenyl | 268° | 63 |
| 21 | 3-methylphenyl | 155° | 60 |
| 22 | 4-methylphenyl | 219° | 77 |
| 23 | 2-trifluoromethylphenyl | 156° | 58 |
| 24 | 2,3-dimethylphenyl | 180° | 69 |
| 25 | 2-ethylphenyl | 100° | 51 |
| 26 | 2-isopropylphenyl | 132° | 47 |
| 27 | 2,3-dimethylphenyl (CH3,CH3) | 183° | 67 |
| 28 | 2-hydroxyphenyl | 284° | 64 |
| 29 | 2-methoxyphenyl | 156° | 36 |
| 30 | naphthyl | 192° | 55 |
| 31 | 2-cyanophenyl | 217° | 40 |

The following 2-aralkyl-6-aryl-imidazo[2,1-b]-1,3,4-thiadiazoles in Table 3 were also prepared in an analogous manner:

TABLE 3

| Example No. | R | R' | F | Yield % of theory |
|---|---|---|---|---|
| 32 | benzyl | phenyl | 150° C. | 63 |
| 33 | benzyl | 4-chlorophenyl | 163° | 77 |
| 34 | benzyl | 4-nitrophenyl | 225° | 57 |
| 35 | 3-chlorobenzyl | phenyl | 117° | 67 |
| 36 | 4-chlorobenzyl | phenyl | 205° | 57 |

TABLE 3-continued

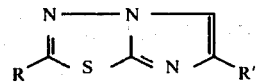

| Example No. | R | R' | F | Yield % of theory |
|---|---|---|---|---|
| 37 |  |  | 170° | 80 |
| 38 |  |  | 169° | 51 |
| 39 |  |  | 176° | 78 |
| 40 |  |  | 201° | 76 |
| 41 |  |  | 129° | 53 |
| 42 |  |  | 125° | 63 |

EXAMPLE 43

2-(2-Methylphenyl)-6-phenyl-imidazo[2,1-b]-1,3,4-thiadiazole

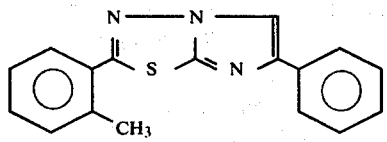

(Process variant A)

(a) 19.1 g (0.1 mol) of 2-amino-5-(2-methylphenyl)-1,3,4-thiadiazole, melting point 193° C., together with 20 g of α-bromoacetophenone are heated to 120° C. in 100 ml of dimethylformamide for 3 hours, whilst stirring. The solvent is largely distilled off, the residue is triturated with water and the precipitate is filtered off and recrystallised from alcohol. 18.6 g, corresponding to 65% of theory, of colourless crystals of melting point 160° C. are obtained.

(b) 19.1 g (0.1 mol) of 2-amino-5-(2-methylphenyl)-1,3,4-thiadiazole together with 20 g of bromoacetophenone are boiled in 200 ml of acetone for 7 hours, whilst stirring. The crystals are filtered off in the cold and heated in boiling water overnight, whilst stirring. The mixture is rendered neutral and the product is filtered off and recrystallised from alcohol, giving a yield of 21 g, corresponding to 72% of theory, of melting point 160° C.

(Process variant B)

4.4 g of 1-(2-methylbenzoylamino)-2-mercapto-4-phenylimidazole (obtained by hydrazinolysis of 2-benzylmercapto-6-phenyl-imidazo[2,1-b]-1,3,4-thiadiazole and subsequent acylation of the 1-amino-2-mercapto-4-phenyl-imidazole with 2-methylbenzoyl chloride), melting point 268°-270° C., were heated to the boil in 30 ml of POCl₃ for 20 minutes. The mixture is cooled and mixed with ice and the product is filtered off and then recrystallised from alcohol. 2.6 g, corresponding to 67% of theory, of colourless crystals of melting point 159°-160° C. are obtained.

The 2-(2-methylphenyl)-6-aryl-imidazo[2,1-b]-1,3,4-thiadiazoles mentioned in Table 4 were obtained according to process variant A, by an analogous procedure:

TABLE 4

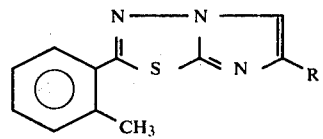

| Example No. | R | F | Yield % of theory |
|---|---|---|---|
| 44 | 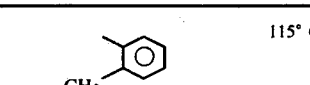 | 115° C. | 27 |
| 45 | 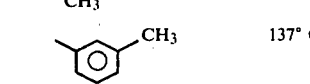 | 137° C. | 67 |
| 46 | 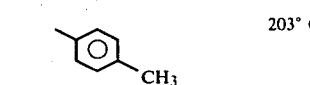 | 203° C. | 60 |
| 47 | 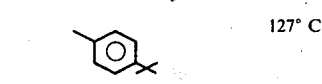 | 127° C. | 65 |
| 48 | 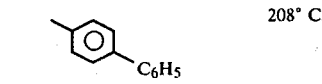 | 208° C. | 60 |
| 49 | 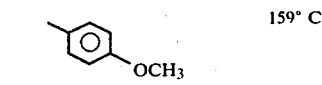 | 159° C. | 42 |
| 50 | 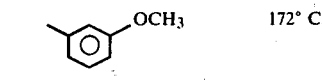 | 172° C. | 64 |
| 51 | 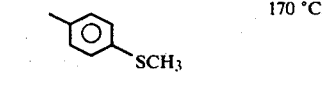 | 170 °C. | 52 |
| 52 | 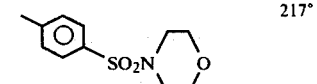 | 217° | 25 |
| 53 | 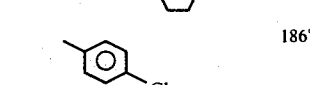 | 186° | 75 |
| 54 | 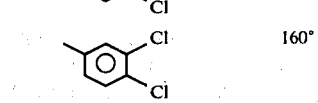 | 160° | 64 |

The following examples of carrying out the invention illustrate the subsequent reactions, which are in themselves known, in which the substituent $R^5$ can be alkylated, acylated, hydrolysed or esterified.

EXAMPLE 55

2-(2-Carboxyphenyl)-6-phenyl-imidazo[2,1-b]-1,3,4-thiadiazole

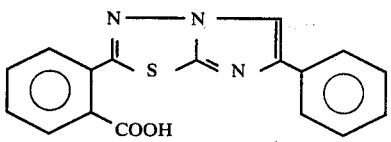

12 g of 2-(2-cyanophenyl)-6-phenyl-imidazo[2,1-b]-1,3,4-thiadiazole (Example No. 31) are heated to 170°–175° C. in 40 g of crystalline $H_3PO_4$ for 5 hours, the mixture is cooled and stirred with water, the precipitate is filtered off and dissolved in 2 N NaOH, the solution is clarified with charcoal and the product is precipitated with 2 N HCl.

The yield is 9.2 g, corresponding to 72% of theory, of colourless crystals of melting point 251° C.

IR spectrum: carboxyl-carbonyl at 1703 $cm^{-1}$; $M^+$ 321

EXAMPLE 56

2-(2-Ethoxycarbonylphenyl)-6-phenyl-imidazo[2,1-b]-1,3,4-thiadiazole

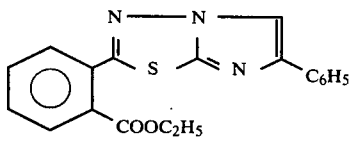

5 g of the compound described in the above example are heated under reflux in 25 ml of thionyl chloride for 2 hours. The thionyl chloride is driven off, the residue is washed with absolute ether, the ether is decanted off and the residue is dissolved in absolute ethanol. The solution is left to stand for 1 hour, the excess alcohol is evaporated off and the amorphous residue is recrystallised from 70% pure ethanol.

2 g of colourless crystals of melting point 112°–114° C. are obtained.

IR spectrum: ester-carbonyl at 1711 $cm^{-1}$.

EXAMPLE 57

2-(Oxymethylenecarbethoxyphenyl)-6-phenyl-imidazo[2,1-b]-1,3,4-thiadiazole

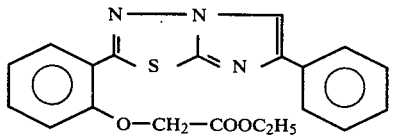

1.2 g of sodium are dissolved in 150 ml of absolute ethanol. 14.6 g of 2-(2-hydroxyphenyl)-6-phenyl-imidazo[2,1-b]-1,3,4-thiadiazole (Example No. 28) are dissolved in this solution and 9 g of bromoacetic acid ethyl ester are then added dropwise, whilst stirring, the mixture being heated under reflux for 2 hours. It is cooled and the crystals are filtered off and washed with water. 9.5 g of colourless crystals, insoluble in alkali, of melting point 120° C. are obtained.

IR spectrum: ester-carbonyl at 1725 $cm^{-1}$.

EXAMPLE 58

The compound of the formula

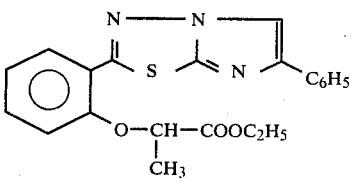

is obtained by reacting 2-(2-hydroxyphenyl)-6-phenyl-imidazo[2,1-b]-1,3,4-thiadiazole with α-bromopropionic acid ethyl ester in an analogous manner. Melting point: 141° C., IR spectrum: ester-carbonyl at 1709 $cm^{-1}$.

EXAMPLE 59

2-(2-Acetoxyphenyl)-6-phenyl-imidazo[2,1-b]-1,3,4-thiadiazole

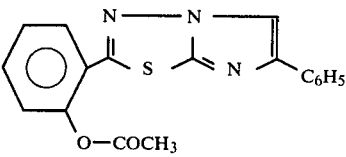

4.6 g of 2-(2-hydroxyphenyl)-6-phenyl-imidazo[2,1-b]-1,3,4-thiadiazole (Example No. 28) are warmed to 150° C. in 75 ml of acetic anhydride for ½ an hour, excess acetic anhydride is evaporated off, the residue is stirred with water and the product is recrystallised from ethanol. 3.8 g, corresponding to 72% of theory, of colourless crystals of melting point 177° C. are obtained.

IR spectrum: no hydroxyl group, ester-carbonyl at 1744 $cm^{-1}$.

EXAMPLE 60

2-Furyl-4-methyl-5-phenyl-imidazo[2,1-b][1,3,4]-thiadiazole

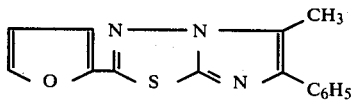

8.4 g of 2-amino-5-furyl-1,3,4-thiadiazole together with 12 g of 2-bromopropiophenone are warmed to 120° C. in 50 ml of dimethylformamide for 4 hours, whilst stirring. The mixture is cooled, water is added and the precipitate is recrystallised from isopropanol. 5 g of colourless crystals of melting point 168° C. are obtained.

EXAMPLE 61

2-(2-Methylphenyl)-4-methyl-5-phenyl-imidazo[2,1-b][1,3,4]-thiadiazole

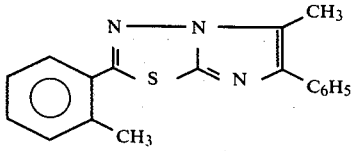

19.1 g of 2-amino-5-(2-methylphenyl)-1,3,4-thiadiazole together with 23.5 g of 2-bromopropiophenone are heated to 120° C. in 200 ml of dimethylformamide for 4 hours.

The mixture is evaporated, water is added to the residue and the product is recrystallised from ethanol.

15 g of colourless crystals of melting point 144° C. are obtained.

Thus, a resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicylic, embonic, nicotinic, methanesulfonic, ethanesulfonic, hydroxy-ethanesulfonic, ethylenesulfonic, benzenesulfonic, halogenbenzenesulfonic, toluensulfonic, naphthalenesulfonic and sulfanilic acid; methionine, tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The present invention also comprises pharmaceutically acceptable bioprecursors of the active compounds of the present invention.

For the purposes of this Specification the term 'pharmaceutically acceptable bioprecursor' of an active compound of the invention means a compound having a structural formula different from the active compound but which nonetheless, upon administration to an animal or human being is converted in the patient's body to the active compound.

What is claimed is:

1. An imidazo-2,1-b]-[1,3,4]-thiadiazole of the formula (I)

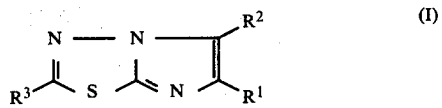

or its therapeutically useful salts in which $R^1$ denotes phenyl, biphenyl or naphthyl each of which is optionally substituted by 1 or 2 identical or different substituents selected from halogen, trifluoromethyl, alkyl or alkenyl with up to 6 carbon atoms, alkoxy with 1 to 6 carbon atoms, nitro, cyano, sulphonamido optionally substituted on the N atom by $C_1$-$C_4$-alkyl and $SO_n$-alkyl (N is 0, 1 or 2) wherein alkyl has 1 to 4 carbon atoms, $R^2$ denotes hydrogen, alkyl or alkenyl with up to 6 carbon atoms or phenyl, biphenyl or naphthyl each of which is optionally substituted by halogen; alkyl, alkenyl or alkoxy each having up to 6 carbon atoms, and $R^3$ denotes naphthyl or furyl, which is optionally substituted by 1 or 2 alkyl radicals having 1 to 6 carbon atoms, or a radical of the formula

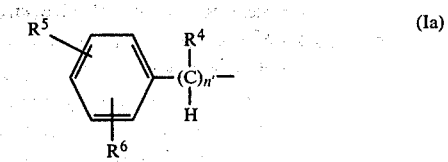

in which n' is 0, or 1, $R^4$ denotes hydrogen or methyl, $R^5$ denotes halogen, alkyl or alkenyl having up to 6 carbon atoms, phenyl or trifluoromethyl, hydroxyl, alkoxy or $SO_{n''}$-alkyl (n'' is 0, 1 or 2) wherein the alkyl portion contains up to 6 carbon atoms, alkanoyloxy with 1 to 4 carbon atoms, alkoxylenecarboxyl with 1 to 4 carbon atoms in the alkyl moiety or alkoxyenecarbalkoxy with 1 to 4 carbon atoms in each alkyl moiety or nitro, cyano, carboxyl or $C_1$-$C_4$-carbalkoxy, and $R^6$ denotes hydrogen or halogen or alkyl, alkenyl or alkoxy each having up to 6 carbon atoms.

2. A compound according to claim 1, in which $R^1$ denotes phenyl, biphenyl or naphthyl each of which is optionally substituted by one or two identical or different substituents selected from halogen, trifluoromethyl, alkyl with 1 to 6 carbon atoms, allyl, alkoxy or $SO_n$-alkyl (n is 0, 1 or 2) with 1 to 4 carbon atoms, nitro, cyano, sulphonamido with an optionally $C_1$-$C_4$-alkyl substituted N atom, and sulphanamido, $R^2$ denotes hydrogen, $C_1$-$C_6$ alkyl, or phenyl, which is unsubstituted or substituted by halogen atom, $C_1$-$C_6$-alkyl, or a $C_1$-$C_6$-alkoxy, and $R^3$ denotes α- or β-furyl, which can be substituted by one or two $C_1$-$C_6$-alkyl radicals, or a substituent of the formula (Ia) as defined in claim 1, in which n' and $R^4$ have the same meanings as in claim 1, $R^5$ has the same meaning as in claim 1 but in which alkenyl is allyl and $R^6$ has the same meaning as in claim 1 but with the exclusion of the alkenyl group.

3. A compound according to claim 2, in which the alkyl substituent on the α- or β-naphthyl or α- or β-furyl, $R^3$ is methyl or ethyl, $R^5$ denotes a substituent selected from fluorine, chlorine, or bromine, methyl, ethyl, propyl, isopropyl, butyl, tert.-butyl, allyl, trifluoromethyl, hydroxyl, methoxy, ethoxy, propoxy, isopropoxy, methylmercapto, isopropylmercapto, methylsulphinyl, methylsulphonyl, ethylsulphonyl, formyloxy, acetoxy, propionyloxy, oxymethylenecarboxyl, α-oxyethylenecarboxyl, oxymethylenecarbomethoxy, oxymethylenecarboethoxy, α-oxyethylenecarbomethoxy, α-oxyethylenecarboethoxy, nitro, cyano, carboxyl, carbomethoxy, carboethoxy and carbopropoxy, and $R^6$ denotes a hydrogen, chlorine or bromine atom or a methyl, ethyl, propyl, butyl, methoxy or ethoxy group.

4. A compound according to claim 1, in which $R^1$ denotes phenyl, which is optionally substituted by fluorine, chlorine, methyl, tert.-butyl, phenyl, trifluoromethyl, methoxy, methylmercapto or methylsulphonyl $R^2$ denotes hydrogen or methyl or phenyl and $R^3$ denotes α- or β-naphthyl or α- or β-furyl in which the furyl group is unsubstituted or substituted by methyl, or a radical of the formula (Ia) as defined in claim 1, in which n' is 0 or 1, $R^4$ denotes hydrogen or methyl, $R^5$ denotes methyl, ethyl, propyl, isopropyl or trifluoromethyl, fluorine, chlorine or bromine or hydroxyl, methoxy, ethoxy, propoxy, oxymethylenecarboxyl, oxymethylenecarbomethoxy, oxymethylenecarboethoxy, α-oxyethylenecarboxyl, α-oxyethylenecarbomethoxy, α-oxyethylenecarboethoxy, methylmercapto, methylsulphonyl, acetoxy, propionyloxy, nitro, cyano, carboxyl, carbomethoxy or carboethoxy and $R^6$ denotes hydrogen, methyl or ethyl, fluorine or chlorine or methoxy or ethoxy.

5. A compound of claim 1 in which
$R^1$ denotes phenyl,
$R^2$ denotes hydrogen, halogen or a lower alkyl and
$R^3$ denotes furyl radical or a of the general formula (Ia) in which
n' is 0 or 1,
$R^4$ denotes hydrogen or methyl,
$R^5$ denotes halogen, $C_1$–$C_4$-lower alkyl and
$R^6$ denotes hydrogen.

6. A compound according claim 1 which is 2-(α-Furyl)-6-phenyl-imidazo[2,1-b]-1,2,4-thiadiazole.

7. A compound according claim 1 which is 2-(2-Methylphenyl)-6-phenyl-imdidazo[2,1-b]-1,3,4-thiadiazole.

8. A compound according claim 1 which is 2-(2-Acetoxyphenyl)-6-phenyl-imidazo[2,1-b]-1,3,4-thiadiazole.

9. A compound according claim 1 which is 2-(2-Methylphenyl)-5-methyl-6-phenyl-imidazo[2,1-b][1,3,4]-thiadiazole.

10. A compound according claim 1 which is 2-(2-Oxy-α-propionic-acid-ethyl-ester)-6-phenyl-imidazo[2,1-b]-1,3,4-thiadiazole.

11. A compound according to claim 1 which is 2-α-Ethylphenyl-6-phenyl-imidazo[2,1-b]-1,3,4-thiadiazole.

12. A pharmaceutical composition containing as an active ingredient an antithrombotically or thrombolytically effective amount of a compound according to claim 1 in admixture with a solid or liquefied gaseous diluent or in admixture with a liquid diluent other than a solvent of a molecular weight less than 200 except in the presence of a surface-active agent.

13. A pharmaceutical composition of claim 12 in the form of a sterile or physiologically isotonic aqueous solution.

14. A composition according to claim 12 or 13 containing from 0.5 to 95% by weight of the said active ingredient.

15. A medicament in dosage unit form comprising an antithrombotically or thrombolytically effective amount of a compound according to claim 1 together with an inert pharmaceutical carrier.

16. A medicament of claim 15 in the form of tablets, pills, dragees, capsules or ampoules.

17. A method of combating thromembolic diseases in warm-blooded animals which comprises administering to the animals a thromembolically effective amount of an active compound according to claim 1 either alone or in admixture with a diluent or in the form of a medicament.

18. A method according to claim 17 in which the active compound is administered parenterally in an amount of 0.01 to 50 mg per kg body weight per day.

19. A method according to claim 18 in which the active compound is administered parenterally in an amount of 0.1 to 10 mg per kg body weight per day.

20. A method according to claim 17 in which the active compound is administered orally in an amount of 0.1 mg to 500 mg per kg body weight per day.

21. A method according to claim 20 in which the active compound is administered orally in an amount of 0.5 mg to 100 mg per kg body weight per day.

* * * * *